United States Patent
Shimaoka

(10) Patent No.: US 6,650,414 B1
(45) Date of Patent: Nov. 18, 2003

(54) METHOD OF MONITORING MICROBE IN WATER

(75) Inventor: Haruo Shimaoka, Nara (JP)

(73) Assignee: Shimadzu Corporation, Kyoto (JP)

( * ) Notice: Subject to any disclaimer, the term of this patent is extended or adjusted under 35 U.S.C. 154(b) by 528 days.

(21) Appl. No.: 09/597,085

(22) Filed: Jun. 20, 2000

(30) Foreign Application Priority Data

Jun. 28, 1999 (JP) .............................. 11-182293

(51) Int. Cl.⁷ .............................................. G01N 21/00
(52) U.S. Cl. ....................................... 356/336; 256/337
(58) Field of Search ................................. 356/336, 338, 356/343, 340, 337

(56) References Cited

U.S. PATENT DOCUMENTS

| 5,379,113 | A | * | 1/1995 | Niwa | 356/336 |
| 5,400,139 | A | * | 3/1995 | Shimaoka | 356/336 |
| 5,796,480 | A | * | 8/1998 | Igushi | 356/366 |
| 5,999,256 | A | * | 12/1999 | Jones et al. | 356/335 |
| 6,091,492 | A | * | 7/2000 | Strickland et al. | 356/336 |
| 6,421,121 | B1 | * | 7/2002 | Haavig et al. | 356/338 |
| 6,473,178 | B2 | * | 10/2002 | Shimaoka | 356/336 |
| 6,496,258 | B1 | * | 12/2002 | Leipertz et al. | 356/336 |
| 6,519,033 | B1 | * | 2/2003 | Quist et al. | 356/337 |

FOREIGN PATENT DOCUMENTS

JP 07325026 A * 12/1995 .......... G01N/15/02

* cited by examiner

Primary Examiner—Frank G. Font
Assistant Examiner—Layla Lauchman
(74) Attorney, Agent, or Firm—Kanesaka & Takeuchi

(57) ABSTRACT

In a method of monitoring specific microbe in water, a monitored object water is supplied into a flow cell provided in a particle size analyzer based on the laser diffraction method, and by irradiating a laser beam to the flow cell, a spatial intensity distribution of the diffraction and scattering light by a group of the particles contained in the monitored object water is measured to obtain a particle size distribution of the group of the particles. Accordingly, information relating to a possibility of an existence of the specific microbe with a known diameter in the monitored object water can be obtained.

6 Claims, 2 Drawing Sheets

METHOD OF MONITORING MICROBE IN WATER

BACKGROUND OF THE INVENTION AND RELATED ART STATEMENT

The present invention relates to a method of monitoring microbe in water, and more particularly, it relates to a monitoring method which is suitable for monitoring an existence or a propagation condition of pathogenic microbe, such as Cryptosporidium, in a water purifying plant.

In recent years, there have been reported examples of group infections to Cryptosporidium in Japan ("Mizujoho" 16(3), PP. 8–11, 1996), and in this report, over sixty percent of seven hundred and several tens of people exposed to protozoa was infected. It is considered that this example was caused due to a contamination of a water receiving vessel in a building, but in Illinois in U.S.A., a large-scaled water-related group infection occurred in 1993 such that 1.6 million people were exposed and 0.4 million people were infected.

According to the above report, Cryptosporidium is a parasitic protozoan (protozoa), and one, which infects healthy person to cause a diarrhea, is a small *C. parvum* which parasitizes in a small intestine. A large *C. muris*, which parasitizes in a stomach of other animals, has been also known. It has been known that *C. parvum* causing a water-related group infection has no specific host, and infects a large range of mammals. Also, Cryptosporidium exists outside the host as an oocyst, and inside the oocyst, there is contained a polypide (sporozoites) which is a main body of the infection to the host. In oocyst, which is an existence configuration of *C. parvum* in question has an ellipsoidal shape close to a sphere having a size (particle diameter) of about 5 μm. Since *C. parvum* is covered by an oocyst wall to protect an inside, it has a strong resistance against a decontaminating chemical or disinfectant, so that it has an extremely high resistance against chlorine used in a water purifying plant. Thus, *C. parvum* has a characteristic that it is difficult to be inactivated by decontamination or sterilization in the water purifying plant.

From the foregoing, even though an example of a massive infection has not been reported at this moment in Japan, there is a very high possibility that when Cryptosporidium exists or is propagated in a raw water reservoir or a clear water reservoir, it is taken into a large number of people to cause infection through a water supply. Thus, it is strongly desired to monitor an existence or propagation condition of Cryptosporidium, but an only method of monitoring Cryptosporidium available now is a method of monitoring a turbidity of water. In this method, although an existence of Cryptosporidium can be recognized in detail by an already-established analytical method, such as fluorescent antibody method, this type of analytical method is very cumbersome, so that it is not realistic to use this method as a regular monitoring method in a water purifying plant or the like. Thus, this method has not been actually used.

Incidentally, in order to strengthen a system of monitoring Cryptosporidium relying only on monitoring the turbidity of water, adopting a fine particulate counter has been considered, but it is difficult to monitor the existence or the propagation condition of Cryptosporidium by this method. Namely, although a monitored object is a pathogenic microbe called "Cryptosporidium", there is an unspecified number of materials in water of the raw water reservoir or the water purifying reservoir, so that all of them are subjected to be measured. Since the fine particulate counter requires a calibration using a specific material, it is difficult to measure all of the particles in water in the water purifying plant wherein the unspecified number of materials exists, accurately. Thus, it is actually impossible to presume or determine an existence or absence of Cryptosporidium.

The present invention has been made in view of the foregoing, and an object of the invention is to provide a method of monitoring microbe in water, wherein water in, such as a raw water reservoir or a water purifying reservoir in the water purifying plant, containing particles of an unspecified number of materials, is the subject to be examined, and information relating to a propagation condition, and an existence or absence of the specific microbe, such as Cryptosporidium, in water can be obtained.

Further objects and advantages of the invention will be apparent from the following description of the invention.

SUMMARY OF THE INVENTION

To achieve the above object, a method of monitoring microbe in water according to the present invention is a method of monitoring an existence or a propagation condition of the specific microbe having a known particle diameter in water, wherein a particle size analyzer on the laser diffraction having a flow cell through which a fluid can flow is used, and object water or liquid to be monitored is guided to an inside of the flow cell continuously or intermittently, to thereby measure a spatial intensity distribution of the diffracted and scattered light obtained by irradiating the laser beam in the flow cell in the condition that the monitored object water flows inside the flow cell. Then, the particle size distribution of the particles existing in the monitored object water is calculated from the measured result, and from the calculated result of the particle size distribution and the substantial particle diameter of the specific microbe which should be monitored, the existence or the propagation condition of the microbe is determined.

In the present invention, by using the particle size analyzer based on the laser diffraction method, a particle size distribution of the particles formed of the unspecified number of materials existing in water is accurately measured, to thereby assume or determine a possibility of an existence of the specific microbe which has a known particle diameter.

Namely, the particle size analyzer base on the laser diffraction method generally measures a spatial intensity distribution of a diffracted and scattered light obtained by irradiating a laser beam to a group of particles which are in a dispersed and flying condition in a medium, and by utilizing a fact that the light intensity distribution follows or relies on the Mie's scattering theory and Frauhhofer's diffraction theory, the particle size distribution of the group of the particles is obtained from the measured result of the spatial intensity distribution of the diffraction and scattering light by the computation based on the Mie's scattering theory and Fraunhofer's diffraction theory. In applying to the present invention, a group of the measured particles is a group of particles formed of various kinds of materials contained in the monitored object water, and the medium is water, so that a measurement is a wet measurement. Namely, the spatial intensity distribution of the diffraction and scattered light, which is obtained by irradiating the laser beam to the flow cell in the condition that the monitored object water flows inside the flow cell, is measured. In this measurement, it is only required that the monitored object water is made to flow in the flow cell continuously, or the monitored object water is made to flow intermittently with a predetermined interval, and the laser beam is irradiated at an adequate timing.

In this particle size analyzer based on the laser diffraction method, if refractive indices of the medium and the measured particle are known, an accurate particle size distribution can be obtained from the measurement result of the spatial intensity distribution of the diffraction and the scattered light. In applying to the present invention, the medium is water, and the refractive index thereof is known. Thus, as to the specific microbe, in case a substantial particle diameter of the microbe is known, even if the refractive index is unknown, a spatial intensity distribution of the diffracted and scattered light of a group of the measured particles formed of the microbe is measured in advance. Then, by setting the refractive index of the group of the measured particles such that the conversion result to the particle size distribution coincides with the known substantial particle diameter of the microbe, the useful refractive index thereof can be presumed.

Accordingly, while the presumed result in regard to the specific microbe is set as the refractive index of the group of the measured particles, the refractive index of water is set as the refractive index of the medium. Then, when a spatial intensity distribution of the diffracted and scattered light by the group of the particles in the monitored object water is converted into the particle size distribution, at least as to the specific microbe, the particle diameter is accurately obtained to reflect in the computed result of the particle size distribution naturally. Thus, if there is a microbe which should be monitored in the monitored to object water, the distribution corresponding to the particle diameter of the microbe should exist in the measured result of the particle size distribution.

Here, in case the existence of the particle corresponding to the particle diameter of the specific microbe is recognized in the group of the particles in the monitored object water, the particle is not always a specific microbe. However, it can be used at least as an index showing a possibility of the existence, and in this case, for example, an alarm may be issued to encourage an operation of the known and detail analysis, such as the fluorescent antibody method.

DETAILED DESCRIPTION OF PREFERRED EMBODIMENTS

Hereunder, preferred embodiments of the invention will be explained with reference to the attached drawings.

Figure 1:
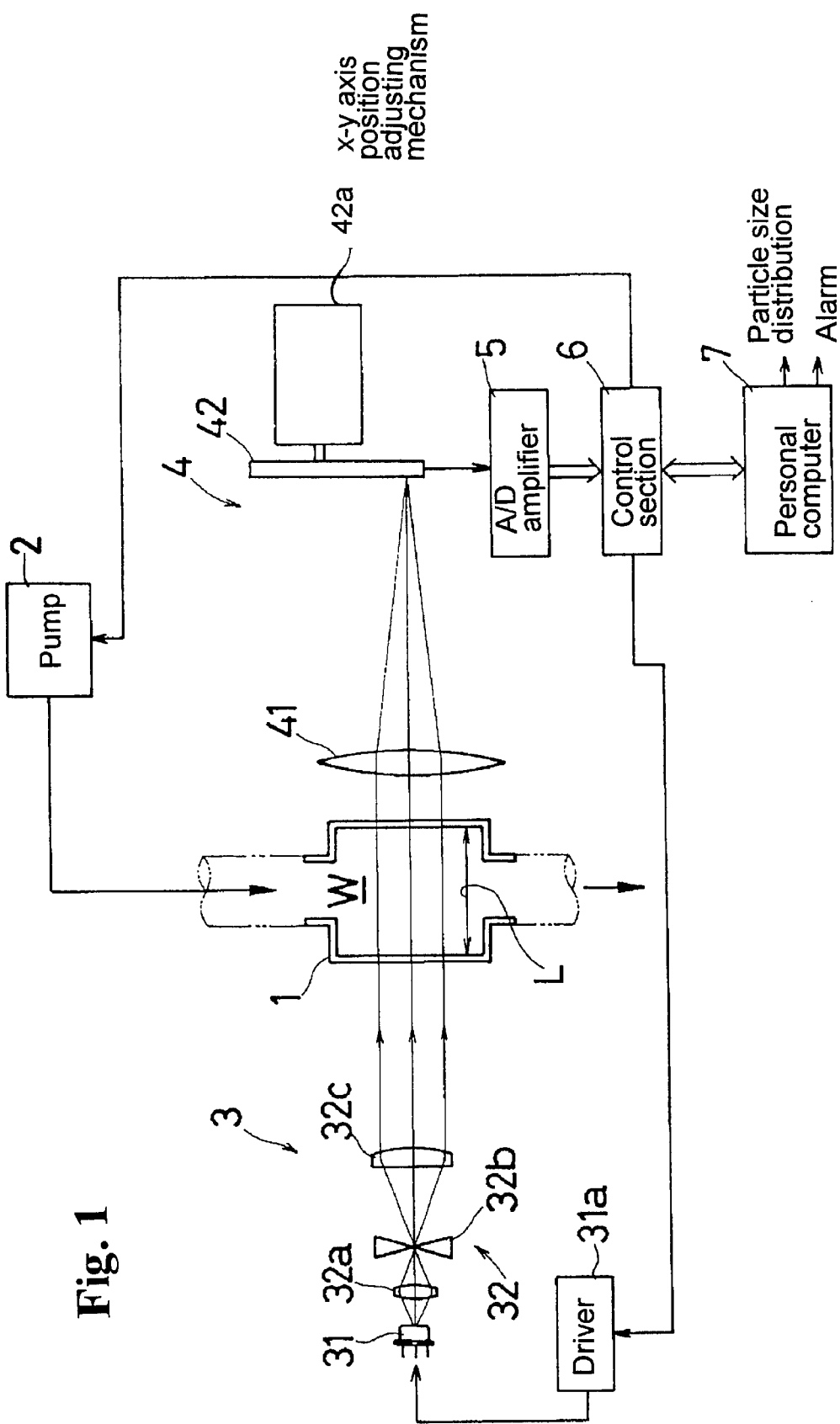
FIG. 1 is a block diagram showing a structure of a microbe monitoring system for Cryptosporidium according to the present invention.

FIG. 1 is a block diagram showing a structure of a microbe monitoring system, in which Cryptosporidium is regarded as an object according to the present invention.

In a flow cell 1, by driving a pump 2 provided in a water purifying reservoir in which object water W to be monitored is stored, object water W is continuously supplied to flow, and through the flow cell 1, water W is again returned to the water purifying reservoir.

To the flow cell 1, a laser beam from a laser irradiation optical system 3 is irradiated. The laser irradiation optical system 3 is formed of a laser diode 31 as a laser beam source, and a beam forming system 32 forming the output light into a parallel luminous flux. The beam forming system 32 is formed of a condenser lens 32a, a space filter 32b, and a collimator lens 32c.

A measuring optical system 4 is disposed at a side opposite to the laser irradiation optical system 3 with respect to the flow cell 1. The measuring optical system 4 is formed of a condenser lens 41, and a diffraction and scattering light sensor 42 disposed at a focal position thereof, as a main system. As the diffraction and scattering light sensor 42, a sensor called a ring detector is used in this embodiment. The diffraction and scattering sensor 42 formed of the ring detector is a known detector in which a large number of light receiving elements having ½ or ¼ ring-shaped light receiving surfaces including different radii, respectively, is disposed without space concentrically around an optical axis of the laser irradiation optical system 3. An alignment of the optical axis is made by driving an x-y axis position adjusting mechanism 42a.

According to the above structure, when the laser beam from the laser irradiation optical system 3 is irradiated to the flow cell 1, the laser beam is diffracted or scattered by a group of particles contained in the object water W flowing in the flow cell 1, and the diffracted and scattered light is condensed by the condenser lens 41, so that a diffracted or scattered image is formed on the light receiving surface of the diffraction and scattering light sensor 42. Therefore, an output of each light receiving element of the diffraction and scattering light sensor 42 as a whole shows a spacial intensity distribution of the diffracted or scattered light by the group of the particles contained in the monitored object water W.

Outputs from the respective light receiving elements of the diffraction and scattering light sensor 42 are amplified and digitalized by an amplifier and analogue-to-digital (A-D) converter 5, and pass through a control section 6 having a communication function to be taken into a personal computer 7 disposed in, for example, a monitoring room. The control section 6 controls the aforementioned pump 2 and a driver 31a for driving the laser diode 31 of the irradiation optical system 3. During the monitoring period, the pump 2 is continuously driven, and the laser diode 31 is driven with an interval set in advance such that the outputs of the respective light receiving elements of the diffraction and scattering light sensor 42 are sampled while the laser diode 31 is being driven.

In the personal computer 7, there is written a computing program, which converts the spatial intensity distribution of the diffracted and scattered light into the particle size distribution of the group of the particles in the monitored object water W by the known computation based on the Mie's scattering theory and Fraunhofer's diffraction theory whenever the spatial intensity distribution of the diffracted and scattered light by the group of the particles in the monitored object water W is taken thereinto through the control section 6. Although this computation requires the refractive index of the measured particles and the refractive index of the medium in which a group of the particles is scattered, since the medium is water, the known refractive index of water is set as it is. Also, the refractive index of the group of the measured particles is set at a value determined by the following method.

Figure 2:
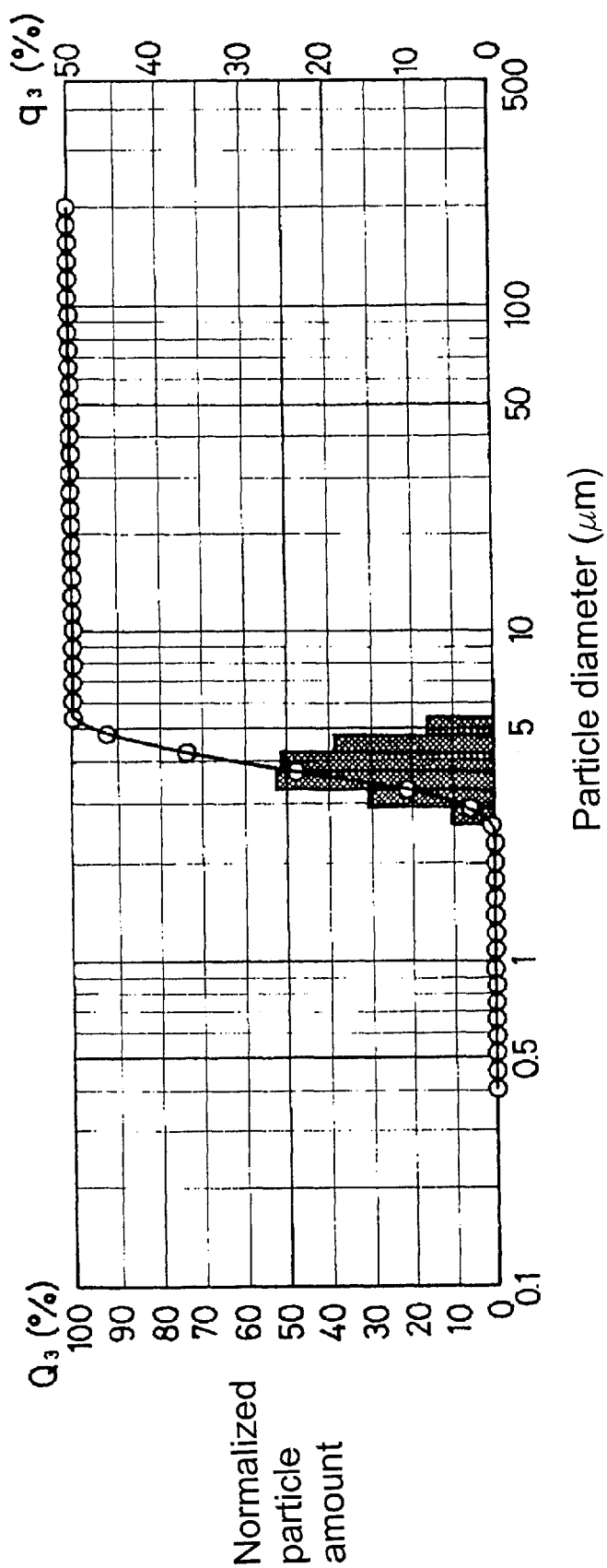
FIG. 2 is a graph showing results of measuring the particle size distribution by a particle size analyzer of FIG. 1, in which Cryptosporidium is actually measured as a measured particle group.

Namely, the refractive index of the group of the measured particles is set such that when a spatial intensity distribution of the diffracted and scattered light regarding only to Cryptosporidium having a particle diameter of about 5 $\mu$m, which is known, as the group of the measured particles, is measured to convert the light intensity distribution into the particle size distribution, the particle size distribution having a peak at approximately 5 μm is obtained. FIG. 2 is a graph showing results of conversion of the spatial intensity distribution of the diffracted and scattered light, which is obtained by irradiating the laser beam to water in the condition that Cryptosporidium as the group of the measured particle is actually scattered in water, into the particle size distribution. A polygonal line graph shows a sieve %, and a bar graph shows a frequency distribution, wherein the refractive index thereof is set such that the particle distribution coincides with the known particle diameter of Cryptosporidium. By setting the refractive index as described above, in case Cryptosporidium exists in the monitored object water, the particle size distribution accurately showing the particle diameter thereof can be obtained.

The structure of the particle size analyzer based on the laser diffraction method as describe above is basically the same as the known particle size analyzer based on the laser diffraction method. However, in case the analyzer is applied to the microbe monitoring system, since a density of the group of the particles to be measured is thin, it is necessary to improve a sensitivity thereof as compared to the normal particle size analyzer based on the laser diffraction method. Therefore, as compared to the particle size analyzer based on the laser diffraction method, an optical path L in the flow cell 1 is elongated to equalize as in the case of substantially increasing the density of the group of the particles. At the same time, in order to decrease a stray light, a multi-coating for anti-reflection is applied to the condenser lens 41, and furthermore, a laser diode of a larger output is used as the laser diode 31 to increase the laser beam strength or intensity. By the setup as describe above, the sensitivity of the analyzer can be improved more than 100 times as compared to the particle size analyzer based on the laser diffraction method normally available or sold in the market.

Incidentally, according to the embodiment of the present invention as described above, object water W stored in the water purifying reservoir or the like is made to flow inside the flow cell 1 continuously, and at the same time, the laser beam is irradiated in the certain intervals. Then, the spatial intensity distribution of the diffracted and scattered light is measured, and the particle size distribution of the group of the particles existing in the monitored object water W is regularly obtained. In case Cryptosporidium exists in the monitored object water, an indication showing an existence of the particles having the particle diameter of approximately 5 μm is shown in the obtained particle size distribution. Accordingly, in the measured results of the particle size distribution regularly obtained, when a peak of approximately 5 μm in the particle diameter or indication showing an existence of the particles having the particle diameter of 5 μm is shown, the personal computer 7 issues an alarm. This alarm does not immediately inform that Cryptosporidium exists in the monitored object water W, but the alarm shows the possibility of existence thereof. Thus, in case the alarm is issued, the monitored object water W is separately sampled, so as to confirm the existence or absence of Cryptosporidium in detail by the known analysis, such as the fluorescent antibody method.

Incidentally, the present invention is not limited to the aforementioned embodiment, and for example, the structure and location of the diffraction and scattering light sensor 42 known already can be used. Also, the monitored object water W may flow in the flow cell 1 not only continuously but also intermittently. Namely, as long as the monitored object water W flows in the flow cell of the particle size analyzer based on the laser diffraction method to measure the particle size distribution of the group of the particles in the monitored object water W, an analyzer formed of any structure can be used.

Also, regarding a microbe which is monitored in the present invention, if a substantial diameter of a microbe is known, any microbe other than Cryptosporidium can be monitored.

As described above, according to the present invention, by guiding object water to be monitored into the flow cell of the particle size analyzer based on the laser diffraction method to thereby measure the particle size distribution of the group of the particles contained in water, an existence or propagation condition of known specific microbe with a known substantial diameter can be monitored in the monitored object water. Thus, the present method can be applied to a method of monitoring harmful microbes, such as Cryptosporidium, so that a monitoring effect can be extremely improved as compared to that of a conventional monitoring method used only by turbidity.

While the invention has been explained with reference to the specific embodiments of the invention, the explanation is illustrative and the invention is limited only by the appended claims.

What is claimed is:

1. A method of monitoring an existence of a specific microbe with a predetermined particle diameter in a liquid, comprising:

providing a particle size analyzer based on a laser diffraction method having a flow cell, guiding a liquid to be monitored into the flow cell, irradiating a laser beam to the flow cell in which the liquid to be monitored flows, measuring a spatial intensity distribution of a diffracted and scattered light of the laser beam, calculating a particle size distribution of particles existing in the monitored liquid from a result of the spatial intensity distribution, and comparing the particle size distribution of the particles in the liquid and the predetermined particle diameter of the microbe obtained in advance to judge if there is a material having the predetermined diameter in the liquid.

2. A method of monitoring according to claim 1, wherein said calculation is made by converting the spatial intensity distribution of the diffracted and scattered light into the particle size distribution based on a refractive index of the measured particles and refractive index of the liquid.

3. A method of monitoring according to claim 2, wherein an optical path in the flow cell is elongated to measure the particles accurately.

4. A method of monitoring according to claim 2, wherein a propagation condition of the specific microbe is monitored by measuring a number of particles.

5. A method of monitoring according to claim 1, further comprising alarming the existence of the material if there is the material having the predetermined diameter in the liquid.

6. A method of monitoring according to claim 1, wherein an existence of Cryptosporidium in a water reservoir is monitored.

* * * * *